United States Patent [19]

Gambale

[11] Patent Number: 5,365,944
[45] Date of Patent: Nov. 22, 1994

[54] GUIDEWIRE EXTENSION WITH SELF-LATCHING DETACHABLE CONNECTOR

[75] Inventor: Richard A. Gambale, Tyngsboro, Mass.

[73] Assignee: C. R. Bard, Inc., Murray Hill, N.J.

[21] Appl. No.: 231,359

[22] Filed: Apr. 19, 1994

Related U.S. Application Data

[63] Continuation of Ser. No. 958,686, Oct. 9, 1992, abandoned.

[51] Int. Cl.⁵ .............................................. A61B 5/00
[52] U.S. Cl. ................................................... 128/772
[58] Field of Search ................ 128/657, 772; 604/95, 604/164, 283; 403/229, 405.1, 406.1, 407.1, 409.1

[56] References Cited

U.S. PATENT DOCUMENTS

| | | |
|---|---|---|
| 642,193 | 1/1900 | Baeumle . |
| 2,105,330 | 1/1938 | Pagenkopf . |
| 3,356,835 | 8/1944 | Duckett . |
| 3,515,027 | 6/1970 | Textrom . |
| 3,517,184 | 6/1970 | Norton et al. . |
| 3,674,014 | 6/1975 | Tilander ............................ 128/657 |
| 3,731,671 | 5/1973 | Mageoh ............................. 128/772 |
| 3,888,598 | 6/1975 | Samiran et al. . |
| 4,080,706 | 3/1978 | Heilman et al. . |
| 4,183,358 | 1/1990 | Cohen . |
| 4,545,390 | 10/1985 | Leary . |
| 4,827,941 | 5/1989 | Taylor et al. ...................... 128/772 |
| 4,875,489 | 10/1989 | Messner et al. ................... 128/772 |
| 5,113,872 | 5/1992 | Jahrmarkt et al. ................ 128/657 |
| 5,133,364 | 7/1992 | Palermro et al. .................. 128/772 |

FOREIGN PATENT DOCUMENTS

| | | |
|---|---|---|
| 0313807 | 5/1989 | European Pat. Off. . |
| 2180454 | 4/1987 | United Kingdom . |

OTHER PUBLICATIONS

Advanced Cardiovascular Systems, Inc. Brochure on DOC Guide Wire Extension dated Mar. 1988.

*Primary Examiner*—Max Hindenburg
*Attorney, Agent, or Firm*—Wolf, Greenfield & Sacks

[57] ABSTRACT

A guidewire system for use in catheter exchanges avoids the need for a separate exchange wire by connecting an extension wire to the proximal end of the guidewire thereby increasing the effective length of the guidewire to permit a catheter exchange. The proximal end of the guidewire is attached to the distal end of the exchange wire by a disconnectible reattachable connection which avoids deformation of the connected joint.

14 Claims, 2 Drawing Sheets

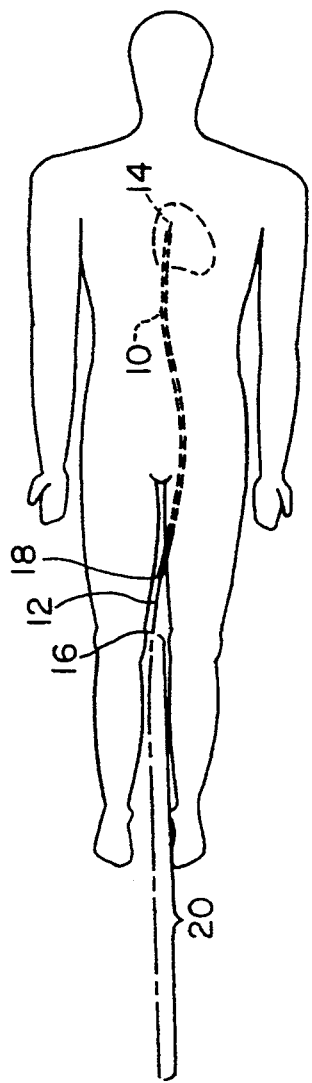
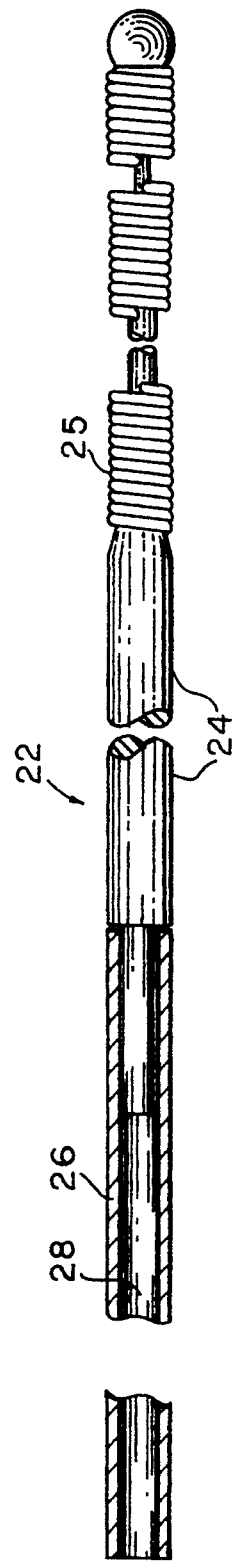
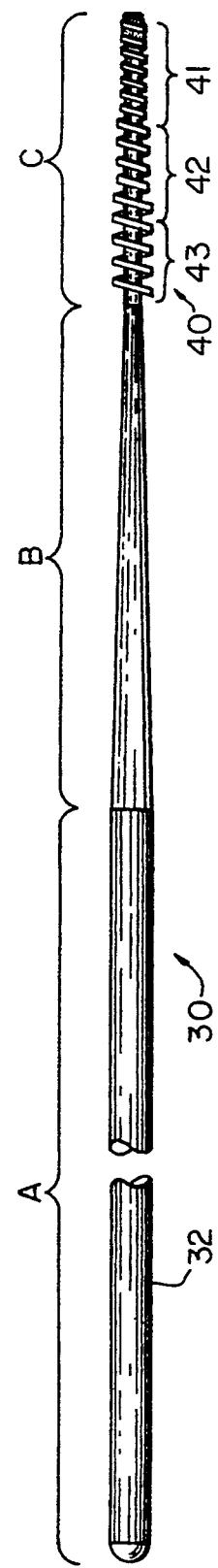

GUIDEWIRE EXTENSION WITH SELF-LATCHING DETACHABLE CONNECTOR

This application is a continuation of application Ser. No. 07/958,686, filed Oct. 9, 1992, now abandoned.

FIELD OF THE INVENTION

This invention relates to guidewires used in guiding of catheters and to devices and techniques for extending the effective length of such guidewires to facilitate catheter exchanges.

BACKGROUND OF THE INVENTION

In some catheterization procedures, it is desirable to use a series of sequentially placed catheters. For example, in percutaneous transluminal coronary angioplasty procedures, in which a balloon catheter is advanced into a stenosed region of the patient's coronary artery and is inflated within the stenosis to dilate the lumen of the artery, it is not uncommon for the physician to require the sequential use of several balloon dilatation catheters having balloons of progressively increasing size. Typically, such catheters are used in connection with a guidewire that extends through the catheter and serves as a guide along which the catheter may be advanced to the stenosis. When performing such a catheter exchange, it is important to do so without significantly shifting the position of the guidewire so that the guidewire may be used to guide the next catheter to the stenosis. In order to maintain guidewire position, conventional practice has been to use a relatively long exchange wire. The exchange wire, which typically is of the order of 300 cm long (as compared to a conventional guidewire length of the order of 175 cm) is first exchanged for the conventional guidewire by removing the conventional guidewire from the indwelling catheter and replacing it with the longer exchange wire. Then the indwelling catheter is withdrawn over the exchange wire, the exchange wire being sufficiently long so that it is never completely covered by the withdrawn catheter, thereby enabling the exchange wire to be held in position by the physician or an assistant during the catheter withdrawal. After the initial catheter is removed, the succeeding catheter is advanced over the exchange wire which guides the second catheter to the stenosis. The exchange wire then may be removed and may be replaced with a conventional length guidewire which, typically, will be more easily manipulated during the continuing angioplasty procedure.

The foregoing procedures are time consuming and somewhat awkward. A significant advance in the technique for effecting catheter exchanges has been developed and has been in use enables exchange of catheters without using separate exchange wires. That system utilizes an extension wire that is attached to the proximal end of the indwelling conventional guidewire. That effectively extends the overall length of the guidewire to that needed for the catheter exchange. The system uses a connection in which the distal end of an extension wire is telescopically connected with the proximal end of the guidewire.

In one such system described in U.S. patent application Ser. No. 07/206,008 filed Jun. 13, 1988, now U.S. Pat. No. 5,133,364, a connection system for a guidewire and guidewire extension utilizes a telescoping connector that is self-latching, disconnectible and reconnectible without deformation of the guidewire or the extension. The connection enables the guidewire extension to be attached for a catheter exchange, then disconnected after the catheter exchange is complete to permit the guidewire and catheter to be manipulated and operated conventionally. Should another catheter exchange be required, the extension wire, which may be reused, is simply reconnected to the proximal end of the guidewire and the catheter exchange procedure may be repeated. The number of guidewire-extension wire connections and disconnections is unlimited as is the number of catheter exchanges that may be performed with the system. More particularly, the guidewire is provided with a tubular socket on the proximal end. The extension wire includes a shaft having a distal end that is dimensioned to be received in the socket. A segment of the distal end of the shaft is surrounded by a helical coil, preferably formed from rectangular cross-section wire. The coil is attached to the extension wire shaft at the distal end of the coil but is free at the proximal end of the coil to enable the coil to stretch and contract about the shaft. The distal end of the extension wire carrying the coil is easily insertable into the socket on the proximal end of the guidewire but self-locks in the socket and cannot be easily withdrawn. The extension wire and guidewire may be disconnected easily, however, by twisting the guidewire extension while simultaneously withdrawing it axially from the socket. The twisting motion frees the locking engagement of the helical coil with the internal surface of the socket.

Although the above-described self-latching reconnectible guidewire system has been used widely by physicians, it would be desirable to improve the convenience of the device. In particular, it is common for guidewires to come in several different diameters, each such guidewire presenting somewhat different operational characteristics. Among the most common diameters for steerable coronary guidewires are those having outer diameters of 0.012" and 0.014". The sockets on the proximal ends of the 0.012" and 0.014" guidewires have different inner diameters and, therefore, each requires a differently dimensioned connector coil on its associated extension wire. Consequently, a separate extension wire must be used with each separate diameter guidewire. That, in turn, requires that different size extension wires be stocked and in readiness for use by the physician. It would be desirable, therefore, to provide an extension wire usable universally with both sizes of guidewires.

SUMMARY OF THE INVENTION

The present invention includes an extension wire having a shaft with a distal segment that is surrounded by a helical coil. The coil is attached to the extension wire shaft at the distal end of the coil and is free at the proximal end of the coil to enable the coil to stretch and contract about the shaft. The coil is provided with three segments including two connective segments that define two operating diameters and a third, most distal segment by which the coil is attached to the shaft. The connector segments include a smaller diameter connective segment adapted to mate with the proximal socket of a smaller diameter guidewire (e.g., 0.012") and a larger diameter (e.g., 0.014") proximal coil segment adapted to engage the socket of a larger diameter guidewire. When used to extend a smaller diameter guidewire, only the smaller diameter connective segment is inserted into the socket of the smaller guidewire. When used in connection with a larger diameter guidewire, the entire coil, including smaller segment, and the larger diameter connective segment are inserted into the socket of the guidewire. Only the larger diameter proximal segment, however, is effective to self-lock to the socket on the proximal end of the guidewire. As with the prior device, the extendable guidewire may be freed from its locking engagement by simultaneously twisting and withdrawing the extension wire from the socket.

It is among the general objects of the invention to provide an improved guidewire extension system.

A further object of the invention is to provide an improved guidewire extension system which is self-latching and which may be used with more than one size of guidewire.

Another object of the invention is to provide an improved connection system for a guidewire and guidewire extension which is disconnectible and reconnectible and which can be used with more than one size of guidewire.

DESCRIPTION OF THE DRAWINGS

The foregoing and other objects and advantages of the invention will be appreciated more fully from the following further description thereof, with reference to the accompanying drawings wherein:

FIG. 1 is a diagrammatic illustration of a patient undergoing catheterization showing the guidewire and, in phantom, the extension wire;

FIG. 2 is a fragmented illustration of a guidewire in accordance with the invention;

FIG. 3 is a fragmented illustration of the extension wire of the invention;

DESCRIPTION OF A PREFERRED EMBODIMENT

Figure 4:
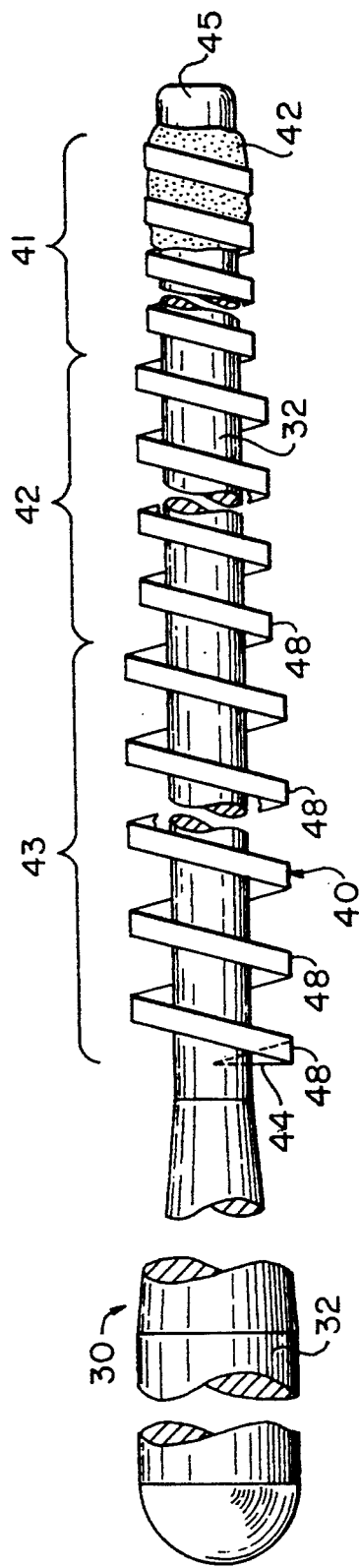
FIG. 4 is a fragmented illustration of the extension wire illustrating the helical coil in enlarged detail.

FIG. 1 illustrates, in highly diagrammatic form, the catheter 10 and guidewire 12 which have been inserted into a patient's femoral artery and have been advanced through the region of the patient's heart where the desired procedure will be performed. The guidewire 12 and catheter 10 will have been inserted and placed in the artery in accordance with well known procedures. When it is desired to perform a catheter exchange, a conventional practice has been to remove the guidewire 12 from the catheter 10 and replace it with a long exchange wire. The catheter 10 then could be removed over the exchange wire and the next catheter could be introduced into the patient over the exchange wire. Then the exchange wire then would be removed and replaced with a shorter, conventional guidewire.

As described in U.S. patent application Ser. No. 07/206,008 filed Jun. 13, 1988, now U.S. Pat. No. 5,133,364 the foregoing procedure has been improved to enable catheters to be exchanged without requiring removal of the guidewire 12 and without requiring the involvement attendant to the use of an exchange wire. In the practice of that technique, the guidewire 12 is connected at its proximal end to an extension wire 20 while the guidewire 12 and catheter 10 remain in the patient. The extension wire 20 is attached securely to the proximal end of the guidewire 12 and serves to extend the effective length of the guidewire 12 sufficiently to permit the catheter 10 to be withdrawn over the guidewire 12 and extension 24.

FIG. 2 shows a guidewire 22 that may be used in accordance with the present invention. The guidewire may be of the type illustrated in U.S. Pat. No. 4,545,390 to Leary having an elongate stainless steel shaft 24 having a proximal end (to the left in FIG. 2) and a distal end (to the right in FIG. 2) with a helical coil 25 mounted at its distal end. The guidewire, alternately, may be of a more conventional construction in which a helical coil extends substantially the full length of the guidewire. The Leary type of guidewire is disclosed by way of example. Such a guidewire may, for example, be of the order of 175 cm long and may have a shaft 24 of a diameter of 0.012" or 0.014", those dimensions being commonly employed at present in the art. In the illustrative embodiment, the proximal end of the shaft 24 is fitted with a tubular member 26 having the same outer diameter of the shaft 24 and defining an elongate internal socket 28. The tubular member 26 may be formed from commercially available hypodermic tubing. It is believed that such tubing has a somewhat roughened internal surface which may enhance the strength of the connection with the extension wire. The dimensions defined by the tubular member 26 and socket 28 depend on the size of the guidewire. For example, in a guidewire of the order of 0.014" outer diameter, the socket may be of the order of 5 cm to 8 cm deep and have an inner diameter of the order of 0.009" to 0.010". The tubular member 26 may have a wall thickness of the order of 0.002". In a smaller diameter guidewire (e.g., 0.012" diameter), the tubular member 26 may define a socket having an inner diameter of the order of 0.007" to 0.008" inner diameter.

FIG. 3 is a fragmented illustration of the extension wire indicated generally by the reference character 30. The extension wire 30 may be considered as having a proximal end (to the left in FIG. 3) and a distal end (to the right in FIG. 3). The overall length of the extension wire 30 may be of the order of 125 cm which, when connected to a guidewire 22 of 175 cm, results in a combined length of 300 cm which corresponds to the length of a conventional exchange wire. The extension wire 30 is formed from an elongate stainless steel shaft 32 that may be considered as being formed of the segments A, B and C as illustrated in FIG. 3. The proximal segment A which may be of the order of 0.011" diameter extends over most of the length of the extension wire 30. The proximal segment A may, for example, be of the order of 102 cm long. The next distal segment B of the shaft is tapered toward the distal end over a length of the order of 1.2 cm and may taper to a diameter of about 0.0044". The cylindrical segment C may be about 1.2 cm long and about 0.0044" diameter.

A helical coil 40 is mounted on the distal cylindrical segment C of the extension wire 30. The helical coil 40 has several segments of different diameters, including a relatively small diameter distal segment 41, a larger diameter intermediate segment 42 and a still larger proximal segment 43. The coil preferably is formed from a high tensile strength material such as type 304 stainless steel. The relaxed inner diameter of the distal segment 41 is substantially the same (within about 0.001") as the diameter of the distal segment C of the shaft. The outer diameter of the distal coil segment 41 is smaller than the inner diameter of the tubular socket 28 on the smaller of the guidewires with which the device is intended to be used so as not to interfere with insertion into or removal from the socket. By way of example for use with a guidewire as small as 0.012" diameter, the distal coil segment 41 may be approximately 0.4 cm long and may have an outer diameter of about 0.006" and an inner diameter of about 0.0046". The next adjacent intermediate coil segment 42 has a relaxed outer diameter that is equal to or just slightly greater than the inner diameter of the tubular socket 28 of the smaller diameter guidewire with which it is intended to be used, to provide a light interfering fit with the socket on that guidewire. By way of example, the coil segment 42 may be approximately 2 mm long and may have an outer diameter of about 0.009" and an inner diameter of about 0.0076". The proximal coil segment 43 has a relaxed outer diameter that is equal to or just slightly greater than the inner diameter of the tubular socket 28 of the larger diameter guidewire with which the extension wire is intended to be used to provide a light interfering fit with the socket on that guidewire. By way of example, in the illustrative example the coil segment 43 may be approximately one millimeter long and may have an outer diameter of 0.0115" and an inner diameter of about 0.0101".

The coil 40 preferably is wound from type 304 stainless steel wire that is of generally flat, rectangular cross-sectional configuration, preferably of the order of 0.0007" thick by 0.003" wide. It may be desirable to form the coil segments 42, 43 so that they are of somewhat tapering diameter, with a slightly larger diameter provided at several of the turns of the proximal end of the coil segment to assure a slight interference fit (of the order of 0.001" to 0.002" in diameter) between the coil segment and the internal surface of the guidewire socket 28 with which it will be used. For example, two or three turns at the proximal ends of one or both of the coil segments 42, 43 may be of slightly enlarged outer diameter of about 0.001".

The distal coil segment 41 is attached at its distal end to the distal segment C of the shaft as by brazing 49, the more proximal portions of the coil segment 41 as well as the more proximal portion of the coil 40 being free to permit the coil 40 to stretch as well as to constrict about the distal shaft segment C. Preferably the coil 40 is of a length and is positioned so that the free proximal end 44 of the coil is not substantially more than 10 mm away from the distal tip 45 of the shaft. Preferably the coil is about 7 mm to 8 mm long.

I have found that the configuration of the distal coil segment 41 and the manner in which it is attached to the shaft is of some importance. Preferably, only several of the most distal coils are of the distal coil segment 30 are brazed to the shaft 32. The remaining more proximal coils of the segment 42 are free to expand or contract longitudinally along the segment C of the shaft. I have found that when the brazed point of attachment is close to the intermediate coil segment 42, the coil may tend to evert when tension is applied to the connection of the coil 40 with the tubular socket 28. When everted, the shaft 30 and distal coil segment 41 may be pulled proximally through one or both of the proximal coils 42, 43, one of which remains locked to the tubular socket. I have found that by brazing the distal coil segment 41 only at several distal coil turns and leaving a substantial number of coil turns unattached to the shaft 32 and free to expand or contract longitudinally, the tendency of eversion is avoided.

The coil is wound on a mandrel having stepped diameters adapted to form the plural diameters for the coil segments. As will be appreciated by those skilled in the art, the coil is wound on a mandrel having a slightly smaller diameter than the intended finished diameter of the coil. When the coil is removed from the winding mandrel it will spring back somewhat to a slightly larger diameter. In the illustrative embodiment, the wire may be wound on a mandrel dimensioned so that the outer diameter of the distal segment 41, as wound, is about 0.0050" diameter, the intermediate segment 42 is of a diameter of 0.0075" and the proximal segment 43 is of a diameter of 0.0090". When removed from the mandrel, the coil segment will relax to outer diameter dimensions of 0.006", 0.009" and 0.0115", respectively. Additionally, it may be noted that in the illustrative embodiment the coils are wound to a predetermined separation of the order of 0.005" between adjacent coils. The coil may be wound to have an aggregate pitch over ten coils of 0.0860" (average 0.0086" per turn). When the coil is released from the mandrel and expands somewhat the pitch between adjacent coils increases slightly. In the case of the largest, proximal coil 43, the pitch may increase from 0.0086" (as wound) to 0.0099" (relaxed).

Figure 5:
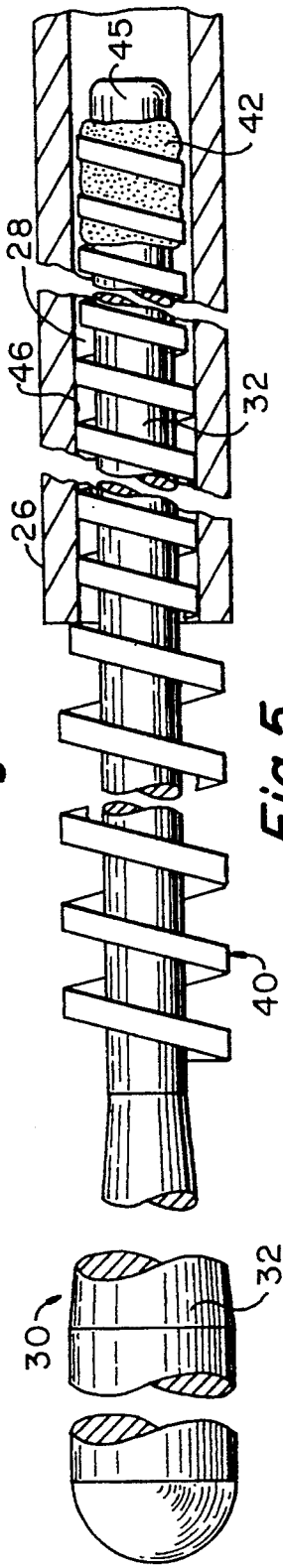
FIG. 5 is an illustration of the connection between the distal end of the extension wire and the proximal end of a guidewire in the smaller range of guidewire sizes.
Figure 6:
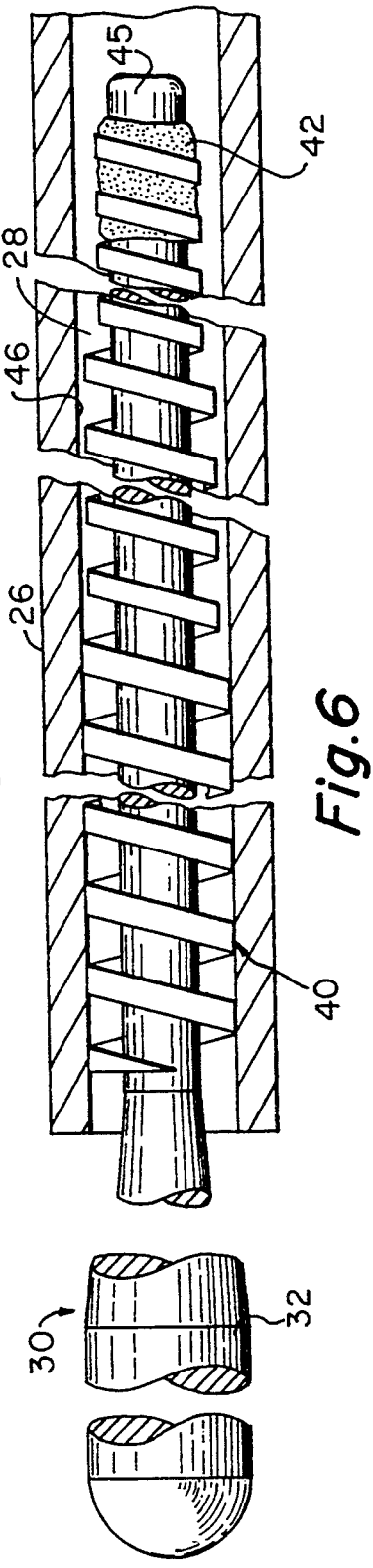
FIG. 6 is an illustration of the connection between the distal end of the extension wire and the proximal end of a guidewire in the larger range of connectible guidewire sizes.

FIGS. 5 and 6 illustrate, respectively, the guidewire extension locked in engagement with a smaller diameter guidewire (e.g., 0.012" diameter) and a larger size guidewire (e.g., 0.014" diameter). In each case, the guidewire extension 30 and guidewire 22 are connected simply by inserting the distal end of the extension 30 into the tubular socket 28 at the proximal end of the guidewire 22. When used with a smaller diameter guidewire (FIG. 5), the coil 40 of the extension wire 30 is inserted into the socket 28 engaging the intermediate coil segment 42 causing the proximal section to elongate substantially as the entire spring is positioned within the hypotube. When used with a larger diameter guidewire (FIG. 6), the full length of the coil, including the still larger proximal segment 43 is inserted into the socket 28. During insertion, at least some of the turns of the coil segment 42 or 43, as appropriate, engage in light interference fit with the internal surface 46 of the tubing 28 to cause the coil 40 to stretch longitudinally which, in turn, causes one or both of the coil segments 42, 43 to constrict to a smaller diameter about the distal shaft segment C, thereby enabling the coil segment to be inserted into the socket 28. Once positioned in the socket, however, the coil segment 42, 43 remains biased toward its expanded configuration which causes the coil segment to bear against the internal surface 46 of the socket 28. The rectangular cross-section of the wire from which the coil 40 is formed thus defines relatively sharp, distinct edges 48 which may engage with the internal surface of the socket 28 to provide a relatively firm connection resistant to axial separation. Thus, the arrangement is self-latching and requires no other manipulation to make the connection. The guidewire and extension described herein provides a connection able to withstand several pounds axial tension.

The guidewire 22 and extension 30 may be easily detached simply by applying a minimal separation force while simultaneously twisting the extension 30 in a direction that will tend to wind or constrict the coil slightly about the distal segment of the guidewire extension. Thus, in the illustrative embodiment the extension 30 would be twisted counterclockwise, as seen from the left in FIG. 4, while withdrawing it axially from the socket 28. The extension 30 and guidewire 22 may be reconnected and disconnected as many times as desired, thus permitting repeated use of the extension wire. The outer diameter of the proximal segment A of the extension wire preferably is not greater than the outer diameter of the largest guidewire 22 with which the extension wire is to be used. The connection made is smooth and continuous and does not provide any impedance to movement of the catheter over the joint.

From the foregoing, it will be appreciated that the invention provides an improved connection system for a guidewire and a guidewire extension and enables the extension to be connected, detached and then reconnected and which permits multiple catheter exchanges should that be desired. The device provides a single extension wire usable with a number of different size guidewires.

It should be understood, however, that the foregoing description of the invention is intended merely to be illustrative thereof and that other modifications, embodiments and equivalents may be apparent to those skilled in the art without departing from its spirit and scope as defined in the appended claims.

Having thus described the invention, what I desire to claim and secure by Letters Patent is:

1. A guidewire extension for telescopic connection with a tubular socket at the proximal end of a medical guidewire comprising:

an elongate flexible shaft having proximal and distal ends;

a self-latching connector element mounted on the distal end of the shaft, the connector element being constructed and arranged to be detachably self-latching to the inner surface of the socket and to be reconnectible after detachment, the connector element being insertable, at least in part, into the socket;

the connector element having at least two distinct, elongate segments, each defining a uniform diameter and extending along the shaft, the more distal segment having a smaller diameter than the proximal segment whereby the distal segment may be inserted into a smaller diameter socket than that into which the proximal segment may be inserted, the proximal segment being insertable into a larger diameter socket;

whereby the extension wire may be detachably connected selectively to guidewires of different sizes.

2. A guidewire extension for telescopic connection with a tubular socket at the proximal end of the medical guidewire comprising:

an elongate flexible shaft having proximal and distal ends;

a self-latching connector element mounted on the distal end of the shaft, the connector element being constructed and arranged to be detachably self-latching to the inner surface of the socket and to be reconnectible after detachment, the connector element being insertable, at least in part, into the socket;

the connector element having at least two segments extending along the shaft, the more distal segment having less cross-sectional dimension than the proximal segment whereby the distal segment may be inserted into a smaller diameter socket than that into which the proximal segment may be inserted, the proximal segment being insertable into a larger diameter socket;

the connector element further comprising a helical coil having a proximal end and a distal end, the coil being attached at its distal end to the region of the distal end of the shaft, the proximal end of the helical coil being free to enable the helical coil to stretch axially and constrict radially about the distal end of the shaft, the portion of the helical coil that defines the distal segment having a smaller diameter than the portion that defines the proximal segment;

whereby the extension wire may be detachably connected selectively to guidewires of different sizes.

3. An extension wire as defined in claim 2 wherein the coil is formed from rectangular cross-section wire.

4. An extension wire as defined in claim 2 wherein the distal portion of the shaft is of reduced diameter, the helical coil being mounted on a reduced diameter portion of the shaft.

5. An extension wire as defined in claim 2 wherein some of the turns at the proximal end of each of the coil segments are of slightly larger diameter than the more distally located turns of the segment.

6. An extension wire as defined in any one of claims 2-5 further comprising:

the helical coil having a distal most segment having a diameter smaller than any of the other coil segments;

the distal most segment being attached to the shaft of the extension wire only at the distal end of the distal most segment.

7. A guidewire for use with a catheter and an extension for the guidewire for enabling multiple catheter exchanges comprising:

a guidewire having a proximal end and a distal end, the guidewire having a socket at its proximal end;

an extension wire having a proximal end and a distal end and including an elongate flexible shaft having proximal and distal ends; a self-latching connector element mounted on the distal end of the shaft, the connector element being constructed and arranged to be detachably self-latching to the inner surface of the socket and to be reconnectible after detachment, the connector element being insertable at least in part into the socket; the connector element having at least two distinct, elongate segments, each defining a uniform diameter and extending along the shaft, the more distal segment having a smaller diameter than the proximal segment whereby the distal segment may be inserted into a smaller diameter socket than that into which the proximal segment may be inserted, the proximal segment being insertable into a large diameter socket;

whereby the guidewire may be detachably connected to said guidewire or to another guidewire having a socket dimensioned to detachably engage the other of the segments of the connector element.

8. A guidewire for use with a catheter and an extension for the guidewire for enabling multiple catheter exchanges comprising:

a guidewire having a proximal end and a distal end, the guidewire having a socket at its proximal end;

an extension wire having a proximal end and a distal end and including an elongate flexible shaft having proximal and distal ends; a self-latching connector element mounted on the distal end of the shaft, the connector element being constructed and arranged to be detachably self-latching to the inner surface of the socket and to be reconnectible after detachment, the connector element being insertable at least in part into the socket; the connector element having at least two segments extending along the shaft, the more distal segment having less cross-sectional dimension than the proximal segment whereby the distal segment may be inserted into a smaller diameter socket than that into which the proximal segment may be inserted, the proximal segment being insertable into a large diameter socket;

the connector element comprising a helical coil having a proximal end and a distal end, the coil being attached at its distal end to the region of the distal end of the shaft, the proximal end of the helical coil being free to enable the helical coil to stretch axially and constrict radially about the distal end of the shaft, the portion of the helical coil that defines the distal segment having a smaller diameter than the portion that defines the proximal segment;

whereby the guidewire may be detachably connected to said guidewire or to another guidewire having a socket dimensioned to detachably engage the other of the segments of the connector element.

9. An extension wire as defined in claim 8 wherein the coil is formed from rectangular cross-section wire.

10. An extension wire as defined in claim 8 wherein the distal portion of the shaft is of reduced diameter, the helical coil being mounted on a reduced diameter portion of the shaft.

11. An extension wire as defined in claim 8 wherein some of the turns at the proximal end of each of the coil segments are of slightly larger diameter than the more distally located turns of the segment.

12. An extension wire as defined in any one of claims 8-11 further comprising:

the helical coil having a distal most segment having a diameter smaller than any of the other coil segments;

the distal most segment being attached to the shaft of the extension wire only at the distal end of the distal most segment.

13. A guidewire extension for telescopic connection with a tubular socket at the proximal end of a medical guidewire comprising:

an elongate flexible shaft having proximal and distal ends;

a self-latching connector element mounted on the distal end of the shaft, the connector element being constructed and arranged to be detachably self-latching to the inner surface of the socket and to be reconnectible after detachment, the connector element being insertable, at least in part, into the socket;

the connector element having at least two distinct locking segments extending along the shaft, the more distal segment having a smaller cross-sectional configuration than the proximal segment whereby the distal segment may be inserted into and locked to a smaller diameter socket than that into which the proximal locking segment may be inserted, the proximal locking segment being insertable into a larger diameter socket;

whereby the extension wire may be detachably connected selectively to guidewires of different sizes.

14. A guidewire for use with a catheter and an extension for the guidewire for enabling multiple catheter exchanges comprising:

the guidewire having a proximal end and a distal end, the guidewire having a socket at its proximal end;

an extension wire having a proximal end and a distal end and including an elongate flexible shaft having proximal and distal ends;

a self-latching connector element mounted on the distal end of the shaft, the connector element being constructed and arranged to be detachably self-latching to the inner surface of the socket and to be reconnectible after detachment, the connector element being insertable at least in part into the socket;

the connector element having at least two distinct elongate locking segments extending along the shaft, the more distal locking segment having smaller cross-sectional dimensions than those of the proximal segment whereby the distal locking segment may be inserted into and locked to a smaller diameter socket than that into which the proximal segment may be inserted, the proximal segment being insertable into and lockable to a large diameter socket;

whereby the guidewire extension may be detachably connected to said guidewire or to another guidewire having a socket dimensioned to detachably engage the other of the segments of the connector element.

* * * * *